United States Patent [19]

Finch

[11] Patent Number: 5,028,427
[45] Date of Patent: Jul. 2, 1991

[54] "CEPHALOSPORIN" COMPOUNDS

[75] Inventor: Stephen C. Finch, Brockham Park, England

[73] Assignee: Beecham Group p.l.c., England

[21] Appl. No.: 235,388

[22] Filed: Aug. 22, 1988

[30] Foreign Application Priority Data

Aug. 22, 1987 [GB] United Kingdom ............... 8719875

[51] Int. Cl.$^5$ ............... C07C 501/57; A61K 31/545
[52] U.S. Cl. ........................... 424/114; 540/221; 540/225; 514/201; 514/203
[58] Field of Search ............... 424/114; 540/225, 221, 540/201, 203

[56] References Cited

U.S. PATENT DOCUMENTS 4,539,149  9/1985  Milner ........................... 540/221

FOREIGN PATENT DOCUMENTS 211656  6/1986  European Pat. Off. .
8520155  8/1985  United Kingdom .

Primary Examiner—Nicholas S. Rizzo
Attorney, Agent, or Firm—Jacobs & Jacobs

[57] ABSTRACT

β-Lactam antibiotics have the formula (Ia) or are pharmaceutically acceptable salts or pharmaceutically acceptable in vivo hydrolysable esters thereof:

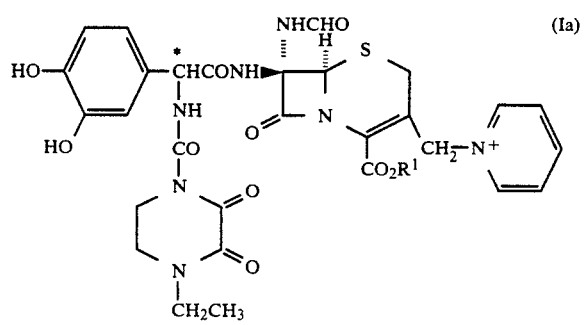

in which the group $CO_2R^1$ is carboxy or a carboxylate anion.

The use of the compounds and processes for their preparation are disclosed.

15 Claims, No Drawings

"CEPHALOSPORIN" COMPOUNDS

This invention relates to a class of novel cephalosporin compounds, which have antibacterial activity and are of value in the treatment of infections in animals, especially mammals including man, caused by a wide range of organisms, particularly Gram-negative organisms. The invention also relates to processes for the preparation of such compounds and to pharmaceutical compositions comprising the antibacterially active compounds.

European Patent Application Number 82303821.1 (Publication Number 0071395) discloses a class of β-lactam antibiotics having an α-formamido (formamidyl) substituent on the carbon atom adjacent to the carbonyl group of the β-lactam ring.

In addition, European Patent Application Publication No. 0 211 656 discloses 7α-formamido cephalosporin derivatives having a substituted pyridinium group in the side-chain attached to the 3-position of the cephalosporin nucleus. In U.K. Patent Application No. GB 8520155 (one of the documents from which a claim to convention priority was made in respect of EP 0 211 656), Example 21 described the preparation of compound (A):

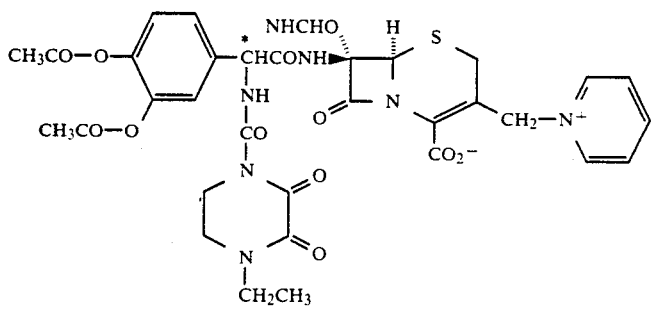

(A)

Surprisingly, it has now been found that 7α-formamido cephalosporins bearing both an unsubstituted pyridinium group in the 3-position side chain and a 3,4-dihydroxyphenyl group in the side-chain attached to the 7-position have outstanding antibacterial properties.

Accordingly the present invention provides a 7α-formamido cephalosporin of formula (I) or a salt thereof:

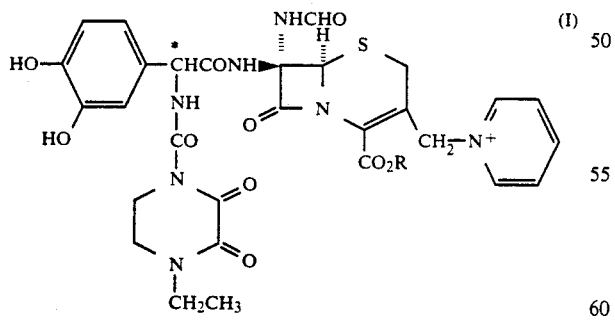

(I)

in which $CO_2R$ is carboxy or a carboxylate anion, or the group R is a readily removable carboxy protecting group.

The compounds of the invention of formula (I) are quaternary salts and the positive charge on the pyridinium moiety must always be balanced by a counter anion. The counter anion may be present on a negatively charged group within the molecule, i.e. the group $CO_2R$ when it represents a carboxylate anion, or the counter anion may be present as an external, inorganic or organic anion.

In compounds of formula (I), the formamido group can exist in conformations wherein the hydrogen atoms of the —NH—CHO moiety are cis- or trans-; of these the cis conformation normally predominates.

The carbon atom marked * in formulae herein is asymmetric and thus compounds of formula (I) may exist as two optically active diastereoisomers. In general the isomer prepared from the D-side chain exhibits the highest antibacterial activity and accordingly the D compound or the DL mixtures are preferred, with the D compound being particularly preferred.

The compounds of formula (I) with the preferred D-side-chain can be separated from a mixture of both diastereoisomers by conventional methods, or prepared from intermediates that bear a D- side chain.

Included within the scope of readily removable carboxy protecting groups for R are, for example, ester groups including pharmaceutically acceptable in vivo hydrolysable ester groups.

Since the β-lactan antibiotic compounds of the present invention are intended for use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

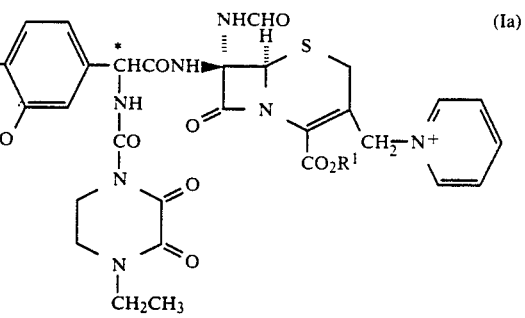

(Ia)

wherein the group $CO_2R^1$ is carboxy or a carboxylate anion.

Non-pharmaceutically acceptable salts of the compound of formula (I) are primarily of use as intermediates in the preparation of a compound of formula (Ia) or a pharmaceutically acceptable salt or pharmaceutically acceptable in vivo hydrolysable ester thereof. Salts within compounds of formula (I) may be prepared by salt exchange in conventional manner.

Similarly, non-pharmaceutically acceptable carboxy-protected derivatives of formula (I) for example certain compounds of formula (I) wherein R is a readily removable carboxy protecting group, may be used as intermediates in the preparation of pharmaceutically acceptable compounds of formula (Ia) or pharmaceutically acceptable salts or pharmaceutically acceptable in vivo hydrolysable esters thereof.

From the foregoing, it will be appreciated that within the quaternary salts of the invention of the formula (I) and (Ia) there exist the sub-groups (Ib) and (Ic) and in vivo hydrolysable esters thereof:

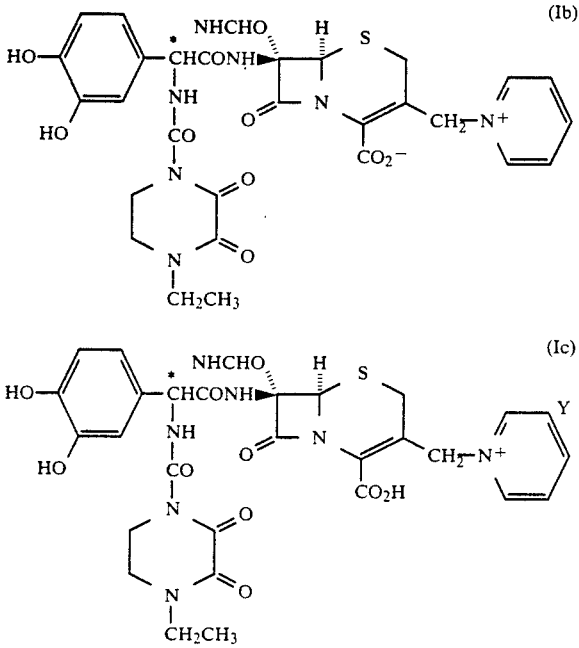

wherein Y is a pharmaceutically acceptable inorganic or organic anion present in the appropriate stoichiometric proportion to balance the positive charge on the pyridinium group.

In a preferred aspect of the invention, the compound of formula (I) is a betaine, i.e. is represented by the formula (Ib). (A betaine is defined as an uncharged species having isolated non-adjacent cationic and anionic sites, and not possessing a hydrogen atom bonded to the cationic site.)

When the compound of the invention of formula (I) or (Ia) may be represented by the formula (Ic), the counter anion Y is suitably derived from an inorganic acid, preferably a mineral acid.

Thus, in formula (Ic), the anion Y may suitably be chloride, bromide, iodide, phosphate (i.e. $\frac{1}{3}$ $PO_4^{3-}$) or sulphate (i.e. $\frac{1}{2}$ $SO_4^{2-}$).

Preferably Y is chloride or sulphate.

Conversion of the betaine of sub-formula (Ib) into salts of sub-formula (Ic) and vice versa may readily be carried out by conventional methods. For example salts of the sub-formula (Ic) may be prepared from the betaine of sub-formula (Ib) by treatment with a dilute mineral acid such as hydrochloric acid.

Quaternary salts within formula (Ic) may also be prepared by salt exchange in a conventional manner, for example by means of an ion-exchange resin.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

When some of the compounds of this invention are allowed to crystallize, or are recrystallized, from organic solvents, solvent of crystallization may be present in the crystalline product. This invention includes within its scope such solvates. Similarly, some of the compounds of this invention may be crystallized or recrystallized from solvents containing water. In such cases water of hydration may be formed. This invention includes within its scope stoichiometric hydrates as well as compounds containing variable amounts of water that may be produced by processes such as lyophilisation.

Suitable readily removable carboxyl protecting groups for the group $-CO_2R$ include groups forming ester derivatives of the carboxylic acid, including in vivo hydrolysable esters. The derivative is preferably one which may readily be cleaved.

Suitable ester-forming carboxyl-protecting groups are those which may be removed under conventional conditions. Such groups for R include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, or an in vivo hydrolysable ester radical such as defined below.

A carboxyl group may be regenerated from any of the above esters by usual methods appropriate to the particular R group, for example, acid- and base-catalyzed hydrolysis, or by enzymically-catalyzed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

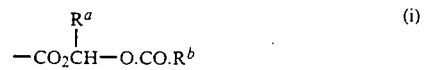

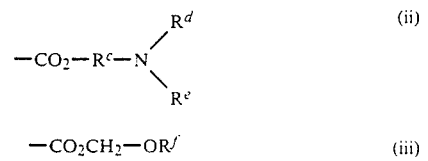

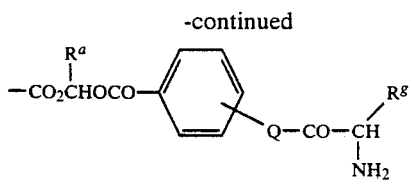

$R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group or a group of formula —$(CH_2)_nCO$— in which n is 1 to 3 and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and Q is oxygen or NH.

Examples of suitable in vivo hydrolysable ester groups include, for example, acyloxyalkyl groups such as acetoxymethyl, pivaloyloxymethyl, α-acetoxyethyl, α-pivaloyloxymethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

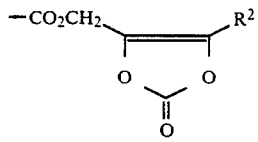

wherein $R^2$ is hydrogen, $C_{1-6}$ alkyl or phenyl.

Specific compounds within this invention include the following and pharmaceutically acceptable salts and in-vivo hydrolysable esters thereof:

7β-[D-2-(3,4-Dihydroxyphenyl)-2-[(4-ethyl-2,3-dioxopiperazin-1-yl)carbonylamino]acetamido]-7α-formamido-3-(pyridinium)methyl-ceph-3-em-4-carboxylate.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a a pharmaceutically acceptable salt or pharmaceutically acceptable in vivo hydrolysable ester thereof together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavoring or coloring agents.

Suppositories will contain conventional suppository base, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as local anesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (70 kg.), for instance 1500 mg per day, depending on the route and frequency of administration. Such dosages correspond to approximately 1.5 to 170 mg/kg per day. Suitably the dosage is from 1 to 6g. per day.

The daily dosage is suitably given by administering a compound of the invention several times in a 24-hour period. For example, 250 mg. is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a pharmaceutically acceptable compound of the invention of formula (Ia) or a pharmaceutically acceptable salt or a pharmaceutically acceptable in vivo hydrolysable ester thereof is administered in the above mentioned dosage range.

The antibiotic compounds according to the present invention may be the sole therapeutic agent in the compositions of the invention or a combination with other antibiotics and/or β-lactamase inhibitor may be employed.

Advantageously the compositions also comprise a compound of formula (II) or a pharmaceutically acceptable salt or ester thereof:

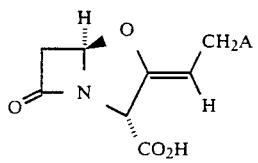

wherein A is hydroxyl; substituted hydroxyl; thiol; a group of formula $SO_2R^3$ wherein $R^3$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises a pharmaceutically acceptable antibiotic compound of the formula (Ia) or a salt or in vivo hydrolysable ester thereof and a pharmaceutically acceptable carrier or excipient together with a β-lactamase inhibitor of formula (III) or a pharmaceutically acceptable salt or in vivo hydrolysable ester thereof:

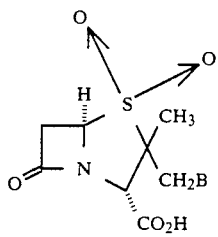

wherein B is hydrogen, halogen or a group of formula:

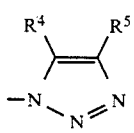

in which $R^4$ and $R^5$ are the same or different and each is hydrogen, $C_{1-6}$ alkoxycarbonyl, or carboxy or a pharmaceutically acceptable salt thereof.

The term 'halogen' refers to fluorine, chlorine, bromine and iodine, and the terms 'halo' and 'halide' are to be construed accordingly.

Further suitable β-lactamase inhibitors include 6-alkylidene penems as described in European Patent Application No. 81301683.9 (Publication Number 0 041 768), and European Patent Application No. 85100521.5 (Publication Number 0 154 132) corresponding to laid open published Danish Patent Application No. 324/85.

Further suitable β-lactamase inhibitors include β-bromopenicillanic acid and salts and in vivo hydrolysable esters thereof and 6β-iodopenicillanic acid and salts and in vivo hydrolysable esters thereof. Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention of the formula (Ia) or a salt or in vivo hydrolysable ester thereof.

The pharmaceutically acceptable antibiotic compounds of the present invention of formula (Ia) or salts or in vivo hydrolysable esters thereof are active against a broad range of Gram positive and Gram negative bacteria, and may be used to treat a wide range of bacterial infections including those in immunocompromised patients.

Amongst many other uses, the pharmaceutically acceptable compounds of the invention of formula (Ia) or salts or in vivo hydrolysable esters thereof are of value in the treatment of respiratory tract and urinary tract infections in humans and may also be used to treat mastitis in cattle. A particular advantage of the antibacterially active compounds of this invention is their stability to β-lactamase enzymes and they are therefore effective against β-lactamase producing organisms.

The present invention further provides a process for the preparation of a compound of formula (I) which process comprises treating a compound of formula (IV) or a salt thereof:

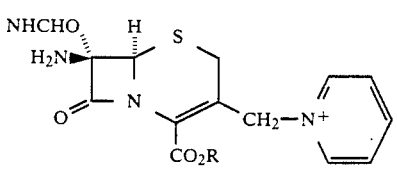

wherein R is as hereinbefore defined, wherein any reactive groups may be protected, and wherein the amino group is optionally substituted with a group which permits acylation to take place; with an N-acylating derivative of an acid of formula (V):

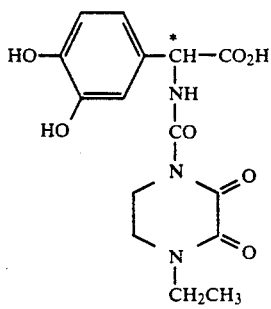 (V)

wherein any reactive groups may be protected; and thereafter, if necessary or desired, carrying out one or more of the following steps:
i) removing any protecting groups;
ii) converting the group —$CO_2R$ into a different group —$CO_2R$; iii) converting the product into a salt.

The compounds of formula (Ia) may be prepared by a similar process, which process further comprises, if necessary, the step of converting the product into a pharmaceutically acceptable salt or a pharmaceutically acceptable in vivo hydrolysable ester.

It will be understood that in the compound of formula (IV) the positive charge on the pyridinium group is balanced by a counter anion which is either external or present on a group within the molecule.

Suitable groups which permit acylation to take place and which are optionally present on the amino group of the starting material of the formula (IV) include N-silyl, N-stannyl and N-phosphorus groups, for example trialkylsilyl groups such as trimethylsilyl, trialkyltin groups such as tri-n-butyltin, groups of formula -$P.R^6R^7$ wherein $R^6$ is an alkyl, haloalkyl, aryl, aralkyl, alkoxy, haloalkyl, aryl, aralkyl, alkoxy, haloalkoxy, aryloxy, aralkyloxy or dialkylamino group, $R^7$ is the same as $R^6$ or is halogen or $R^6$ and $R^7$ together form a ring; suitable such phosphorus groups being —$P(OC_2H_5)_2$, —$P(C_2H_5)_2$,

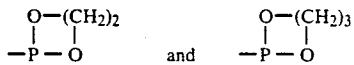

When used herein the term "aryl" includes phenyl and naphthyl optionally substituted with up to five fluorine, chlorine, $C_{1-6}$ alkyl, $C_{1-6}$ alkoxy, halo ($C_{1-6}$)alkyl, hydroxy, amino, carboxy, $C_{1-6}$ alkoxycarbonyl, aryloxycarbonyl, $C_{1-6}$ alkoxycarbonyl($C_{1-6}$)alkyl, nitro, aryloxycarbonyloxy, aryl $C_{1-6}$ alkyloxycarbonyloxy, $C_{1-6}$ alkyloxycarbonyloxy, $C_{1-6}$ alkylcarbonyloxy, arylcarbonyloxy, aryl $C_{1-6}$ alkylcarbonyloxy, or aryl $C_{1-6}$ alkyloxycarbonyl groups.

A preferred group which permits acylation to take place is trimethylsilyl which may suitably be introduced in situ, prior to acylation, by causing an appropriate silylating reagent, e.g. trimethylsilyl chloride, to react with the compound of formula (IV).

The silylation reaction may suitably be carried out in an inert anhydrous solvent, for example dichloromethane, in an inert atmosphere, preferably under argon. An organic base, for example N,N-dimethylaniline, may be added to facilitate the reaction. The reaction is normally carried out at an elevated temperature, suitably 30°–60° C.; preferably 40°–50° C.

A reactive N-acylating derivative of the acid (V) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)- 1,2-alkylene oxide such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (V) or a salt or a reactive derivative thereof with a halogenating (e.g. chlorinating or brominating) agent such as phosphorus pentachloride, thionyl chloride, oxalyl chloride or phosgene.

Alternatively, the N-acylating derivative of the acid (V) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric, phosphorus, and phosphinic acids) or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (V) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (V) with an oxime.

Other reactive N-acylating derivatives of the acid (V) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$ - $C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (V) is to treat the acid of formula (V) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (V) so derived may then be caused to react with a compound of formula (IV). The acylation reaction may conveniently be carried out at $-40°$ to $+30°$ C., if desired in the presence of an acid binding agent such as pyridine. A catalyst such as 4-dimethylaminopyridine may optionally also be added. A preferred solvent for the above acylation reaction is dichloromethane.

A preferred intermediate of formula (IV) has the formula (IVA):

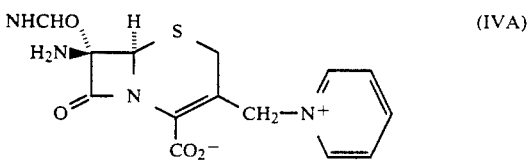

Accordingly, a preferred process for the preparation of a compound of formula (I) comprises treating a compound of formula (IVA) as hereinabove defined, wherein any reactive groups may be protected, and wherein the amino group is optionally substituted with a group which permits acylation to take place; with an N-acylating derivative of an acid of formula (V):

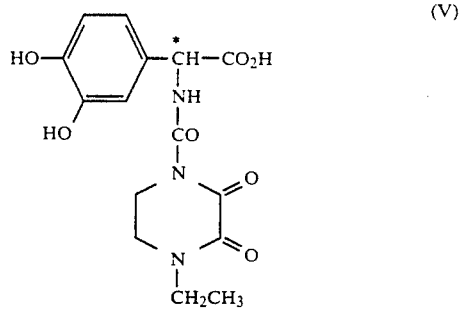

wherein any reactive groups may be protected; and thereafter, if necessary or desired, carrying out one or more of the following steps:

i) removing any protecting groups;
ii) converting the group $-CO_2-$ into a group $-CO_2R$;
iii) converting the product into a salt.

The compounds of formula (Ia) may be prepared by a similar process, which process further comprises, if necessary, the step of converting the product into a pharmaceutically acceptable salt or a pharmaceutically acceptable in vivo hydrolysable ester.

A further preferred intermediate of formula (IV) as hereinabove described has the formula (VI) or is an acid addition salt thereof:

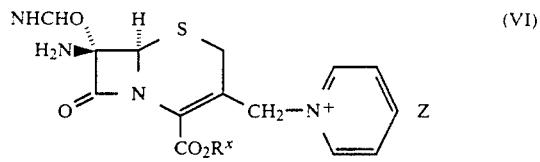

wherein $R^x$ is hydrogen or a readily removable carboxy protecting group; and Z is an inorganic or organic anion present in the appropriate stoichiometric proportion to balance the positive charge on the pyridinium group.

Suitable readily removable carboxy protecting groups for $R^x$ include those listed hereinabove as suitable readily removable carboxy protecting groups for R.

The compounds of formula (I) may therefore also suitably be prepared by reacting a compound of formula (VI) as hereinabove defined or an acid addition salt thereof, wherein any reactive groups may be protected with an N-acylating derivative of an acid of formula (V) as hereinbefore defined (wherein any reactive groups may be protected); and thereafter, if necessary or desired, carrying out one or more of the following steps:

i) removing any protecting groups;
ii) converting the group $R^x$ into a group R;
iii) converting the product into a salt.

For the compound of formula (VI) to react with an N-acylating derivative of an acid of formula (V) it may first be necessary to introduce on to the amino group in the compound of formula (VI) a group which permits acylation to take place. Suitable such groups for this purpose include those listed hereinabove as being optionally present on the amino group in the compound of formula (IV) prior to acylation.

A preferred group which may be introduced onto the amino group in the compound of formula (VI) is trimethylsilyl. Advantageously the silylation reaction may be carried out in situ, prior to the acylation reaction, with a silylating agent that does not require concomitant addition of base. Suitable silylating agents include, for example, N-(trimethylsilyl)acetamide, N,O-bis(trimethylsilyl)acetamide, N,O-bis (trimethylsilyl)trifluoroacetamide, N-methyl-N-trimethylsilylacetamide, N-methyl-N-trimethylsilyltrifluoroacetamide, N,N'-bis(trimethylsilyl)urea, and N,O-bis(trimethylsilyl)carbamate. A preferred silylating agent is N-(trimethylsilyl)acetamide. The silylation reaction may suitably be carried out in an inert, anhydrous organic solvent such as tetrahydrofuran, acetonitrile or dichloromethane at room temperature or at an elevated temperature, for example 30–60° C., preferably 40–50° C. The above process may optionally be carried out in the presence of a small quantity, for example 0.1 equivalents, of a silyl halide, for example a tri($C_{1-6}$)alkylsilyl halide, especially trimethylsilyl chloride.

Preferred values of Z in compounds of formula (VI) are chloride and bromide.

As noted above, a reactive N-acylating derivative of the acid (V) is employed in the preparation of a compound of formula (I) from a compound of formula (VI), the choice of reactive derivative being influenced by the chemical nature of the substituents of the acid of formula (V).

Suitable N-acylating derivatives of the acid (V) include those listed hereinbefore as suitable for use in the process for preparing a compound of formula (I) from a compound of formula (IV). Methods for preparing such suitable N-acylating derivatives are as hereinabove described.

A preferred N-acylating derivative of the acid of formula (V) is an acid halide, most preferably the acid chloride, which advantageously may be freshly prepared from the corresponding acid (V) before use. Suitable halogenating agents for preparing acid halides from the acid of formula (V) are hereinbefore described.

Preferred halogenating agents include oxalyl chloride, thionyl chloride, and phosgene.

In formula (VI) the group $CO_2R^x$ is preferably carboxy. Other preferred groups for $R^x$ are diphenylmethyl (benzhydryl), 4-methoxybenzyl, and tri ($C_{1-6}$ alkyl)silyl, especially trimethylsilyl. The trimethylsilyl group may suitably be introduced onto the 4- carboxy group using silylating agents listed hereinabove as suitable for silylating the amino group in compounds of formula (VI).

In the processes described hereinabove and in those described hereinbelow, reactive groups may be protected (and the protecting groups subsequently cleaved) by methods known in the art, for example those described in "Protective Groups in Organic Synthesis" by T. W. Greene (Wiley-Interscience, N.Y., 1981).

It will be understood that one or both of the hydroxy groups in the dihydroxyphenyl group may be protected in such processes. When both hydroxy groups are protected it will be further understood that a different protecting group may be used for each hydroxy group, although, more conveniently, the protecting groups used will be the same.

Particularly suitable protecting groups for the hydroxy groups in the 3,4-dihydroxyphenyl group include those which afford esters, carbonates and ethers (including silyl ethers).

Examples of suitable hydroxy protecting groups include formyl and optionally substituted $C_{1-6}$ alkylcarbonyl and arylcarbonyl groups such as acetyl, chloroacetyl, dichloroacetyl and benzoyl; optionally substituted $C_{1-6}$ alkoxycarbonyl and aryl $C_{1-6}$ alkoxycarbonyl, for example ethoxycarbonyl, trimethylsilylethoxycarbonyl, benzyloxycarbonyl and 4-nitrobenzyloxycarbonyl; and optionally substituted $C_{2-6}$ alkenyloxycarbonyl such as allyloxycarbonyl.

Further examples of suitable hydroxy protecting groups include aryl, aryl $C_{1-6}$ alkyl, optionally substituted $C_{1-6}$ alkyl, optionally substituted $C_{2-6}$ alkenyl, optionally substituted $C_{3-7}$ cycloalkyl, and silyl groups.

Some examples of optional substituents in protecting groups mentioned hereinabove as being optionally substituted include up to three groups (which may be the same or different) chosen from halogen, hydroxy, $C_{1-6}$ alkoxy, $C_{1-6}$ alkylthio, cyano, nitro, carboxy, carboxylic acid $C_{1-6}$ alkyl ester, carbamoyl, amino, mono ($C_{1-6}$) alkylamino, and di ($C_{1-6}$) alkylamino.

Preferred alkyl protecting groups include, for example, methyl or ethyl, optionally substituted with ($C_{1-6}$) alkoxy or ($C_{1-6}$) alkylthio, for example with methoxy, ethoxy, or methylthio. Further useful protecting groups are methoxyethoxymethyl and (trimethylsilyl)ethoxymethyl. The hydroxy groups may be protected by an alkylene bridge so that the 3,4-dihydroxyphenyl group becomes, for example, 3,4-methylenedioxyphenyl, 3,4-ethylenedioxyphenyl, or 3,4-[1,1-dimethyl(methylenedioxy)]phenyl.

Preferred aryl $C_{1-6}$ alkyl protecting groups include benzyl and 4-nitrobenzyl.

Preferred silyl protecting groups may be substituted with $C_{1-6}$ alkyl and/or phenyl groups and include, for example, trimethylsilyl, t-butyldimethylsilyl, t-butyldiphenylsilyl, triethylsilyl, isopropyldimethylsilyl, triphenylmethyldimethylsilyl and the like. The resulting silyl ethers may be cleaved by methods known in the art, such as those described by T. W. Greene (loc. cit.) or by M. Lalonde and T.H. Chan in Synthesis, 1985 (September), pages 817-845 and references therein.

Particularly preferred hydroxy protecting groups are acetyl and trimethylsilyl.

When it is necessary to remove protecting groups, deprotection may be carried out by any convenient method known in the art that does not cause unwanted side reactions to occur to any appreciable extent. Methods that are particularly suitable for converting the 3,4-diacetoxyphenyl group into the 3,4-dihydroxyphenyl group include treatment with aqueous sodium sulphite solution or aqueous sodium hydrogen carbonate solution, or treatment with an esterase, especially citrus acetylesterase. When the dihydroxyphenyl group is protected as a silyl ether, for example the trimethylsilyl ether, removal of the silyl group is normally carried out by acid hydrolysis.

The compounds of formula (IV) herein which are, inter alia, intermediates for the compounds of formula (I) as hereinbefore defined may be prepared by reacting a compound of formula (VII) or acid addition salt thereof:

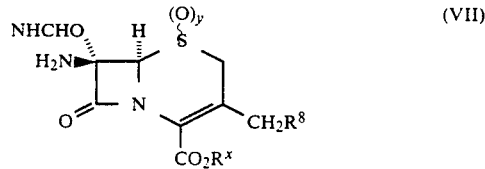

wherein $R^x$ is as hereinbefore defined, $R^8$ is a leaving group and y is 0 or 1; with pyridine or a pyridinium salt, with the proviso that when pyridine is used and $R^8$ is an acyloxy group, the group $CO_2R^x$ must be in the free acid form or a salt thereof; and thereafter if necessary:

i) converting the group $R^x$ into a group R;
ii) converting a sulphoxide (wherein y is 1) into a sulphide (wherein y is 0) by methods known in the art;
iii) converting the product into a salt.

Suitable leaving groups $R^8$ include halide or an acyloxy group such as, for example the acetoxy group.

Preferably $R^8$ is an acetoxy group or a bromine or iodine atom.

A preferred pyridinium salt which may be used in the above process is N-trimethylsilyl pyridinium iodide, i.e. the adduct of pyridine and trimethylsilyl iodide (compare D.G. Walker et al., J. Orc. Chem., 1988, 53, 983-991).

Compounds of the formula (VII) may be prepared as described in European Patent Application Publication No. 0 071 395.

When $R^8$ is an acetoxy group, the conversion of compounds of formula (VII) into compounds of formula (IV) is preferably carried out in an aqueous medium, if necessary with a water-miscible organic solvent such as acetone present to give a homogeneous solution. The reaction may suitably be conducted in the presence of an alkali metal iodide, e.g. sodium iodide, or an alkali metal thiocyanate, e.g. potassium thiocyanate, and is generally carried out at an elevated temperature, for example between 40° and 80° C., and preferably at about 60° C.

When the reaction is complete (as adjudged, for example, by an analytical method such as reversed phase HPLC), the product may be isolated by chromatography on 7 a suitable resin, for example 'Diaion HP 20SS' resin (obtained from Mitsubishi Chemical Corporation).

Acid addition salts of the compound of formula (VI) as hereinbefore defined may suitably be prepared by reacting a compound of formula (VI) with an appropriate acid, preferably a mineral acid.

In an alternative aspect, the acid addition salt of the compound of formula (VI) as hereinbefore defined may suitably be prepared by reacting a compound of formula (IVA) with an appropriate acid, for example hydrochloric acid or sulphuric acid; and also, if necessary or desired, converting the carboxy group into a group $CO_2R^x$.

The above reactions may suitably be carried out in an aqueous medium at ambient temperature by addition of a dilute mineral acid, generally in the presence of a water-miscible organic solvent such as acetone, ethanol, propan-1-ol or propan-2-ol.

The reaction mixture may be chilled to 0°–10° C., generally to less than 5° C., to facilitate isolation of the product.

The compounds of formula (I) may also suitably be prepared by reacting a compound of formula (VIII):

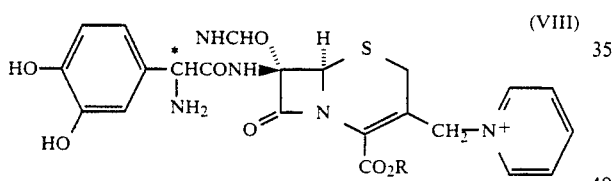
(VIII)

wherein R is as defined with respect to formula (I); the α-amino group is optionally substituted with a group which permits acylation to take place; and any reactive groups may be protected; with an N-acylating derivative of an acid of formula (IX):

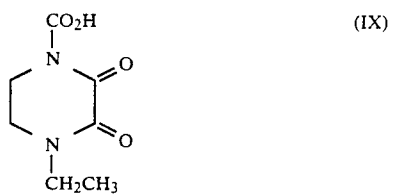
(IX)

and thereafter, if necessary or desired, carrying out one or more of the following steps:

i) removing any protecting groups;
ii) converting the group —$CO_2R$ into a different group —$CO_2R$;
iii) converting the product into a salt.

Compounds of formula (VIII) above which are, inter alia, intermediates for the compounds of formula (I) may be prepared by reacting compounds of formula (IV) as hereinbefore defined with an N-acylating derivative of an acid of formula (X):

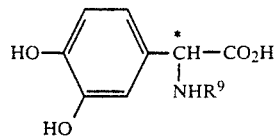
(X)

wherein $R^9$ is an amino protecting group, and thereafter removing protecting group $R^9$.

Suitable amino-protecting groups $R^9$ are those well known in the art which may be removed under conventional conditions without disruption of the remainder of the molecule.

Examples of amino-protecting groups for $R^9$ include benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl optionally substituted by up to three halogen atoms, for example tert-butoxycarbonyl and 2,2,2-trichloroethoxycarbonyl; benzyloxycarbonyl optionally substituted as for benzyl above; allyloxycarbonyl; or trityl.

Compounds of formula (VIII) may also be prepared by reacting a compound of formula (IV) as hereinbefore defined with an N-acylating derivative of an c-azido acid of formula (XI):

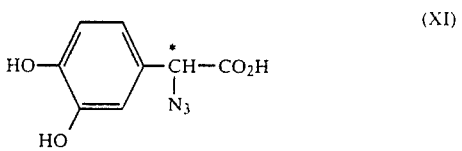
(XI)

followed by reduction of the azido group to an amino group by conventional methods, for example by catalytic hydrogenation or by reaction with triphenylphosphine followed by hydrolysis of the resultant phosphinimine.

Compounds of formula (VIII) may also be prepared by reaction of a compound of formula (IV) as hereinbefore defined with an N-acylating derivative of an acid of formula (XII):

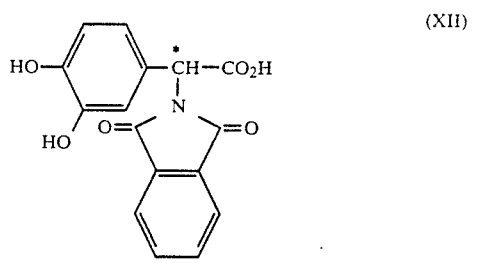
(XII)

and thereafter converting the phthalimido group into an amino group by conventional methods.

The present invention further provides a process for the preparation of a compound of formula (I) which process comprises treating a compound of the formula (XIII):

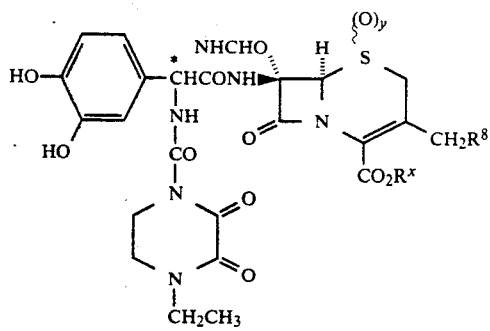

(XIII)

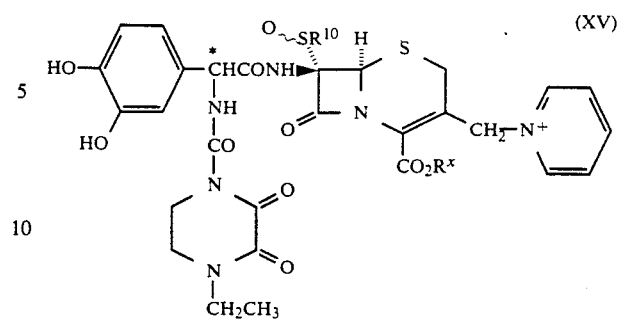

(XV)

$R^x$, $R^8$, y, and * are as hereinbefore defined and wherein any reactive groups may be protected; with pyridine or a pyridinium salt with the proviso that when pyridine is used and $R^8$ is an acyloxy group, the group $CO_2R^x$ must be in the free acid form or a salt thereof; and thereafter if necessary:

i) converting the group $R^x$ into a group R;

ii) converting a sulphoxide (wherein y is 1) into a sulphide (wherein y is 0) by methods known in the art;

iii) removing any protecting groups;

iv) converting the product into a salt.

Suitable leaving groups $R^8$ include halide or an acyloxy group such as, for example, the acetoxy group.

Preferably $R^8$ is an acetoxy group or a bromine or iodine atom.

A preferred pyridinium salt which may be used in the above process is N-trimethylsilyl pyridinium iodide.

The present invention also provides a process for the preparation of a compound of formula (I) which process comprises treating a compound of the formula (XIV):

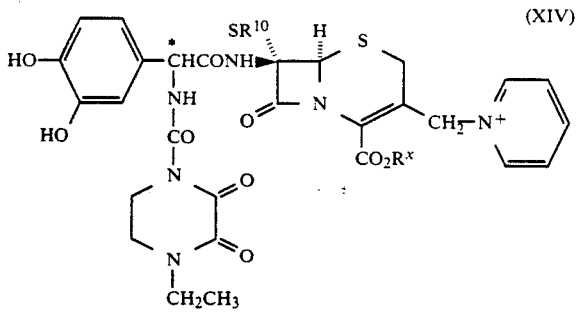

(XIV)

wherein any reactive groups may be protected, $R^x$ is hydrogen or a readily removable carboxy protecting group; and $R^{10}$ is $C_{1-6}$ alkyl, aryl or benzyl; with a heavy metal ion such as mercury, silver, thallium, lead or copper; and thereafter in situ with a nucleophilic derivative of formamide; and thereafter, if necessary, carrying out one or more of the following steps:

i) removing any protecting groups;

ii) converting the group $R^x$ into a group R;

iii) converting the product into a salt;

The above process is analogous to that described in European Patent Application No. 84300338.5 (Publication Number 0 115 405).

In an alternative aspect, the present invention provides a process for the preparation of a compound of formula (I) which process comprises treating a compound of formula (XV):

wherein *, $R^x$ and $R^{10}$ are as defined for formula (XIV) and wherein any reactive groups may be protected; with a nucleophilic derivative of formamide; and thereafter, if necessary, carrying out one or more of the following steps.

i) converting the group $R^x$ into a group R;

ii) removing any protecting groups; and iii) converting the product into a salt;

The present invention further provides a process for the preparation of a compound of formula (I) which process comprises formylating a compound of formula (XVI):

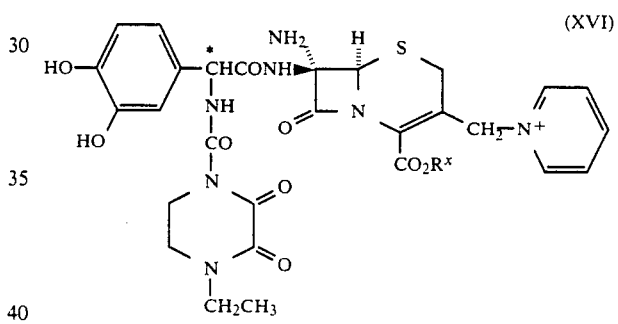

(XVI)

wherein $R^x$, and * are as hereinbefore defined and wherein any reactive groups may be protected; and thereafter, if necessary, carrying out one or more of the following steps.

i) removing any protective groups;

ii) converting the group $R^x$ into a group R;

iii) converting the product into a salt.

Suitable formylating agents include the reagent 4-formyl-2-methyl-1,3,4-thiadiazolin-5-thione (see H. Yazawa and S. Goto, *Tetrahedron Letters*, 1985, 26 3703–3706), or mixed anhydrides such as formic acetic anhydride. The reaction may suitably be carried out in a temperature in the range −50° C. to −30° C. in aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

One process for preparing compounds within formula (XVI) is disclosed in or is analogous to processes disclosed in European Patent Application No. 82303821.1 (Publication Number 0 071 395).

A further process for preparing compounds within formula (XVI) comprises treating a compound of formula (XV) with ammonia.

It will be apparent from the above that a process for preparing compounds of formula (I) comprises formamidylating a compound of formula (XVII):

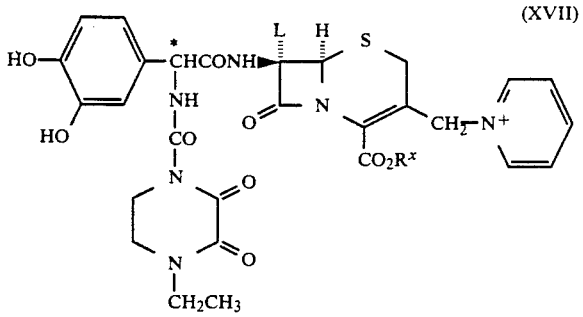

(XVII)

wherein L is SR¹⁰, SOR¹⁰ or NH₂; and R$^x$, R¹⁰ and * are as hereinbefore defined.

As used herein the term 'formamidylating' denotes converting the group L into the group —NHCHO.

The antibiotic compounds of the present invention have excellent pharmacokinetic properties and are active against a wide range of Gram-negative and Gram-positive organisms including *E. coli* such as, for example, ESS, JT4, JT425 and NCTC 10418; *Pseudomonas Spp.* such as *Ps. aeruginosa* for example 10662 and Dalgleish; *Serratia marcescens* US32; *Serratia marcescens* HCN 3956; *Klebsiella pneumoniae* A and T767; *Enterobacter cloacae* N1; *Enterobacter cloacae* P99; *P. mirabilis* such as, for example C977 and 889; *P. morganii; P. rettgeri; B. subtillis; Staph.aureus* such as, for example Oxford and Russell; *N.catarrhalis* 1502; *Bacteroides fragilis; H. influenzae* and β*-Haemolytic Strep.*CN10.

The following Examples illustrate the preparation and biological activity of the compounds of the present invention.

EXAMPLE 1

7β-[D-2-(3,4-Dihydroxyphenyl)-2-[(4-ethyl-2,3-dioxopiperazin-1-yl)carbonylamino]acetamido]-7β-formamido-3-(pyridinium)methyl-ceph-3-em-4-carboxylate (a)

7β-Amino-7β-formamido-3-(pyridinium)methylceph-3em-4-carboxylate

7β-Amino-7α-formamidocephalosporanic acid (0.6g) (prepared as described in European Patent Application Publication No. 0 211 656) in water (10 ml) containing sodium iodide (2.00 g; 13.3 mmol) and pyridine (0.978 g; 12.4 mmol) was heated at 60° C. The reaction was monitored by reverse phase HPLC. After ca. 4.5 h, purification as in Example 2(a) of European Patent Application publication No. 0 211 656 afforded the title compound (0.3 g; 64%); μ$_{max}$ (KBr) 3400, 3280, 1765, 1670, and 1610cm⁻¹; δ$_H$ (D₂O) (major rotamer) 3.13 and 3.59 (together 2H, ABq, J 18Hz), 5.21 (1H, s), 5.36 (2H, AA' system), 8.08 (2H,m), 8.15 (1H, s), 8.56 (1H,m), and 8.89 (2H,m); [F.A.B. (+ve ion) (diamylphenol/CHCl₃)MH³⁰ 335].

(b)

7β-[D-2-(3,4-Diacetoxyphenyl)-2-[(4-ethyl-2,3-dioxopiperazin-1-yl)carbonylamino]acetamido]-7g-formamido-3-(pyridinium)methyl-ceph-3-em-4-carboxylate 7β-Amino-7α-formamido-3-(pyridinium)methyl-ceph-3-em-4-carboxylate (167 mg; 0.5 mmol) in dry dichloromethane (10 ml) containing N,N-dimethylaniline (485 mg; 4.0 mmol) and trimethylchlorosilane (217 mg; 2.0 mmol) was refluxed for 1h. The mixture was cooled and a solution of D-2-(3,4-diacetoxyphenyl)-2-[(4-ethyl-2,3-dioxopiperazin-1-yl)carbonylamino]acetyl chloride (freshly prepared from the corresponding acid (326 mg; 0.75 mmol) via the method described in Example 2(b) of European Patent Application publication number 0 211 656) in dry dichloromethane (10 ml) was added with stirring at room temperature.

The reaction mixture was diluted with dichloromethane and extracted with water (x3). The combined aqueous extracts were washed with dichloromethane (x2). The aqueous phase was concentrated at reduced pressure and the concentrate was chromatographed on HP20SS resin, eluting first with water, then acetone/water mixtures. The product-containing eluant was concentrated at reduced pressure, then lyophilised to give the title compound (170 mg; 42% ca. 3:1 D/L isomers); λ$_{max}$ (H₂O) 255 nm (ε$_m$ 16122); ν$_{max}$ (KBr) 3420, 1770, 1710 (sh), 1680, and 1620 cm⁻; δ$_H$(D₂O) (D isomer; major rotamer) 1.17 (3H, t, J 7.2 Hz), 2.26 (3H, s) 2.29 (3H, s), 2.75 and 3.38 (together 2H, ABq, J 17.6 Hz), 3.49 (2H, q, J, 7.2 Hz), 3.57-3.80 (2H, m), 3.80-4.10 (2H, m), 5.21 and 5.43 (together 2H, ABq, J 14.7 Hz), 5.34 (1H, s), 5.51 (1H, s), 7.15-7.55 (3H, m), 8.00-8.13 (2H, m), 8.15 (1H, s), 8.50-8.66 (1H, m), and 8.80-9.00 (2H, m); [F.A.B. (+ve ion) (Diamylphenol/CHCl₃) MH+752].

(c)

7β-[D-2-(3,4-Dihydroxyphenyl)-2-[(4-ethyl-2,3-dioxopiperazin-1-yl)carbonylamino]acetamido]-7α-formamido-3-(pyridinium)methyl-ceph-3-em-4-carboxylate To a stirred solution of 7β-[D-2-(3,4-diacetoxyphenyl)-2-[(4-ethyl-2,3-dioxopiperazin-1-yl)carbonylamino]acetamido]-7α-formamido-3-(pyridinium)-methyl-ceph-3-em-4-carboxylate (100 mg, 0.13 mmol) in water (ca. 3 ml) was added 2.5% (w/v) aqueous sodium carbonate solution to pH 8.0 followed by sodium sulphite (42 mg, 0.33 mmol) in water (ca. 1 ml). The pH of the mixture was maintained at 9.0 throughout the reaction by further additions of 2.5% (w/v) aqueous sodium carbonate. The reaction was monitored by reverse phase hplc, and after 1 h the mixture was purified by Diaion "HP20SS" chromatography eluting with water/acetone mixtures. The product containing eluant was concentrated and then lyophilised to give the title compound (62 mg; 70%; ca. 6:1 D/L isomer mixture); λ$_{max}$ (H₂O) 252 nm (ε$_m$ 18,250); ν$_{max}$ (KBr) 3285, 1780, 1710 (sh), 1676, and 1617cm⁻; δ$_H$ (D₂O) (D isomer; major rotamer) 1.56 (3H, t, J 7.1 Hz), 2.83 (1H, d, J 17.7 Hz, higher field arm of ABq), 3.30-3.55 (3H, m), 3.55-3.75 (2H, m), 3.80-4.05 (2H, m) 5.10-5.50 (4H, m), 6.70-7.00 (3H, m), 7.90-8.02 (2H, m), 8.13 (1H, s), 8.55 (1H, t, J 7.4 Hz), and 8.83 (2H, d, J 5.4 Hz); [F.A.B. (+ve ion) (thioglycerol) MH+ 668].

EXAMPLE 2

7β-[D-2-(3,4-Dihydroxyphenyl)-2-[(4-ethyl-2,3-dioxopiperazin-1-yl)carbonylamino]acetamido]-7α-formamido-3-(pyridinium)methyl-ceph-3-em-4-carboxylate 7β-Amino-7α-formamido-3-(pyridinium)methyl-ceph-3-em-4-carboxylate (0.207 g; 0.62 mmol) (prepared as in Example 1(a)) in dry dichloromethane (10 ml) containing trimethylchlorosilane (0.4 g; 3.7 mmol) and N,N-dimethylaniline (0.6 g; 5 mmol) was heated at reflux, with stirring, for 1.25 h. The mixture was cooled, D-2-[3,4-bis(trimethylsilyloxy)phenyl]-2-[(4-ethyl-2,3-dioxopiperazin-1-yl)carbonylamino]acetyl chloride (0.477 g; 0.93 mmol) (prepared as described in European Patent Application Publication No. 0 219 926A) in dry dichloromethane (10 ml) was added and the mixture stirred for 2 h. The reaction mixture was diluted with dichloromethane and extracted with water (x3). After ca. 15 min the combined aqueous extracts were adjusted to pH 7 with saturated aqueous sodium hydrogen carbonate. Chromatography on HP20SS resin, eluting first with water, then acetone/water mixtures gave after concentration and lyophilisation the title product (0.127 g; 30%).

EXAMPLE 3

Minimum Inhibitory Concentration (MIC) values of the compound of Example 1 (product of step (c)) against *Enterobacter cloacae* P99, *Serratia marcescens* US32, *Serratia marcescens* HCN 3956, *Pseudomonas aeruginosa* NCTC 10662 and *Staphylococcus aureus* Oxford were determined by serial dilution in a nutrient agar (Oxoid). The plates were inoculated with $10^4$ colony forming units and incubated overnight at 37° C. The MIC values recorded in Table 1 were the lowest concentration of antibiotic to inhibit growth. Comparative data for 7β-[D-2-(3,4-diacetoxyphenyl)-2-[(4-ethyl-2,3-dioxopiperazin-1-yl)carbonylamino]acetamido]-7α-formamido-3-(pyridinium)methyl-ceph-3-em-4-carboxylate (Compound A) are also given. The latter compound (product of Example 1, step (b)) was prepared in U.K. patent application GB 8520155 (Example 21) which was one of the applications from which priority was claimed in European Patent Application No. 86306064.6 (Publication No. 0 211 656).

TABLE 1

MIC data

| ORGANISM | MIC (μg/ml) | |
|---|---|---|
| | Compound A | Example 1 |
| *Enterobacter cloacae* P 99 | 8 | 2 |
| *Serratia marcescens* US 32 | 0.5 | 0.12 |
| *Serratia marcescens* HCN 3956 | 16 | 2 |
| *Pseudomonas aeruginosa* NCTC 10662 | 2 | 0.5 |
| *Staphylococcus aureus* Oxford | 16 | 8 |

What is claimed is:

1. A compound of formula (I) or a salt thereof:

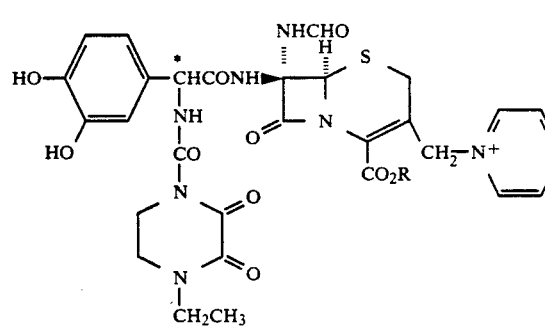

in which $CO_2R$ is carboxy or a carboxylate anion, or the group R is a readily removable carboxy protecting group.

2. A compound of formula (Ia) or a pharmaceutically acceptable salt or pharmaceutically acceptable in vivo hydrolyzable ester thereof:

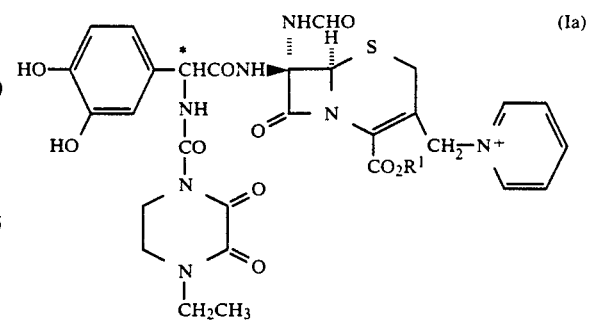

wherein $CO_2R^1$ is carboxy or a carboxylate anion.

3. The compound according to claim 1 which is 7β-[D-2-(3,4-Dihydroxyphenyl)-2-[(4-ethyl-2,3-dioxopiperazin-1-yl)carbonylamino]acetamido]-7α-formamido-3-(pyridinium)methyl-ceph-3-em-4-carboxylate.

4. A pharmaceutical composition useful for treating bacterial infections in humans and animals which comprises an antibacterially effective amount of a compound of the formula I

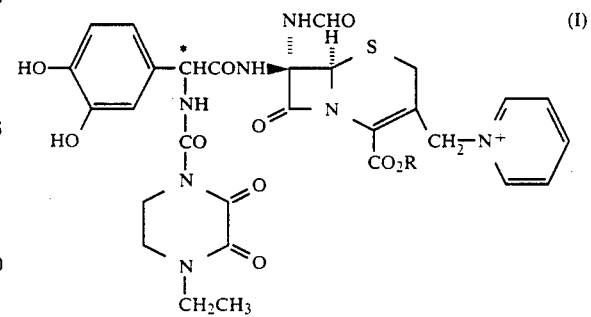

or a pharmaceutically acceptable salt thereof in which $CO_2R$ is carboxy or a carboxylate anion, or the group R is a readily removable carboxy protecting group, in combination with a pharmaceutically acceptable carrier.

5. A pharmaceutical composition useful for treating bacterial infections in humans and animals which comprises an antibacterially effective amount of a compound of the formula (Ia)

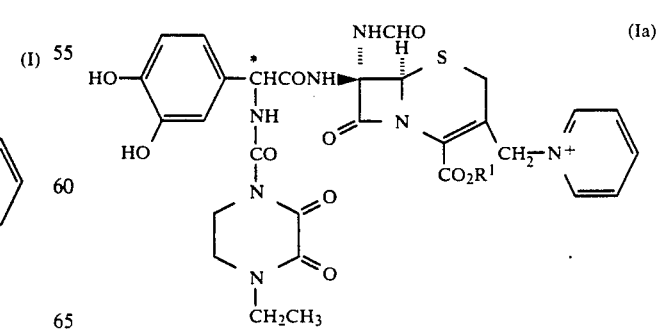

a pharmaceutically acceptable salt thereof or a pharmaceutically acceptable in vivo hydrolyzable ester thereof wherein $CO_2R^1$ is carboxy or a carboxylate anion, in combination with a pharmaceutically acceptable carrier.

6. A composition according to claim 4 wherein the compound is 7β-[D-2-(3,4-Dihydroxyphenyl)-2-[(4-ethyl-2,3-dioxopiperazin-1-yl)car-bonylamino]acetamido]-7α-formamido-3-(pyridinium)-methyl-ceph-3-em-4-carboxylate.

7. A method of treating bacterial infections in humans and animals which comprises administering to a human or animal in need thereof an antibacterially effective amount of a compound of the formula (I)

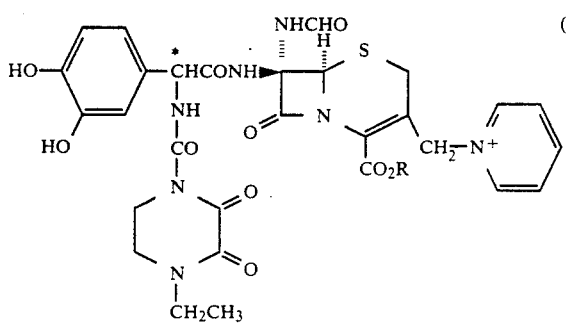

or a pharmaceutically acceptable salt thereof in which $CO_2R$ is carboxy or a carboxylate anion, or the group R is a readily removable carboxy protecting group, in combination with a pharmaceutically acceptable carrier.

8. A method of treating bacterial infections in humans and animals which comprises administering to a human or animal in need thereof an antibacterially effective amount of a compound of the formula (Ia)

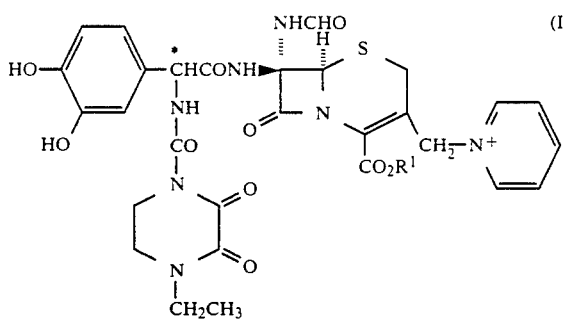

a pharmaceutically acceptable salt thereof or a pharmaceutically acceptable in vivo hydrolyzable ester thereof wherein $CO_2R^1$ is carboxy or a carboxylate anion, in combination with a pharmaceutically acceptable carrier.

9. A method according to claim 7 wherein the compound is 7β-[D-2-(3,4-Dihydroxyphenyl)-2-[(4-ethyl-2,3-dioxopiperazin-1-yl) carbonylamino]acetamido]-7α-formamido-3-(pyridinium)methyl-ceph-3-em-4-carboxylate.

10. A pharmaceutical composition useful for treating bacterial infections in humans and animals which comprises an antibacterially effective amount of a compound of the formula I

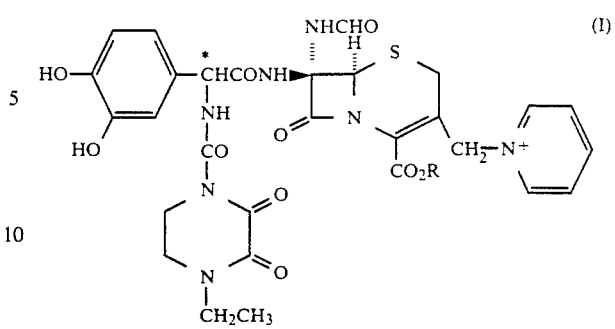

or a pharmaceutically acceptable salt thereof in which $CO_2R$ is carboxy or a carboxylate anion, or the group R is a readily removable carboxy protecting group and a β-lactamase inhibitory amount of a β-lactamase inhibitor, in combination with a pharmaceutically acceptable carrier.

11. A pharmaceutical composition useful for treating bacterial infections in humans and animals which comprises an antibacterially effective amount of a compound of the formula (Ia)

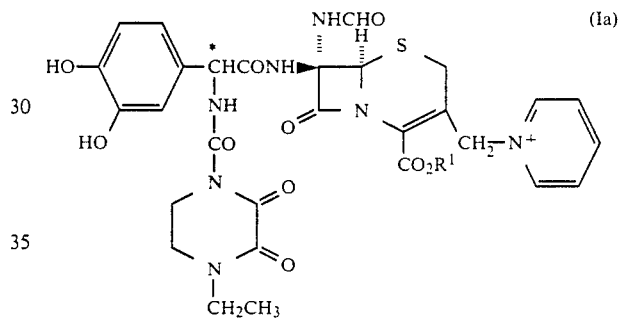

a pharmaceutically acceptable salt thereof or a pharmaceutically acceptable in vivo hydrolyzable ester thereof wherein $CO_2R^1$ is carboxy or a carboxylate anion and a β-lactamase inhibitory amount of a β-lactamase inhibitor, in combination with a pharmaceutically acceptable carrier.

12. A composition according to claim 10 wherein the compound is 7β-[D-2-(3,4-Dihydroxyphenyl)-2-[(4-ethyl-2,3-dioxopiperazin-1-yl)car-bonylamino]acetamido]-7α-formamido-3-(pyridinium)-methyl-ceph-3-em-4-carboxylate.

13. A method of treating bacterial infections in humans and animals which comprises administering to a human or animal in need thereof an antibacterially effective amount of a compound of the formula (I)

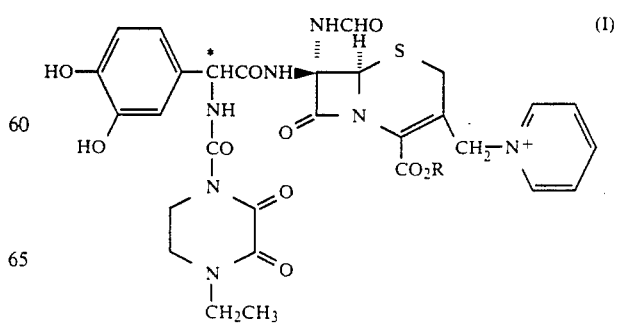

or a pharmaceutically acceptable salt thereof in which CO₂R is carboxy or a carboxylate anion, or the group R is a readily removable carboxy protecting group and a β-lactamase inhibitory amount of a β-lactamase inhibitor, in combination with a pharmaceutically acceptable carrier.

14. A method of treating bacterial infections in humans and animals which comprise administering to a human or animal in need thereof an antibacterially effective amount of a compound of the formula (Ia)

(Ia)

a pharmaceutically acceptable salt thereof or a pharmaceutically acceptable in vivo hydrolyzable ester thereof wherein CO₂R¹ is carboxy or a carboxylate anion and a β-lactamase inhibitory amount of a β-lactamase inhibitor, in combination with a pharmaceutically acceptable carrier.

15. A method according to claim 13 wherein the compound is 7β-[D-2-(3,4-Dihydroxyphenyl)-2-[(4-ethyl-2,3-dioxopiperazin-1-yl)carbonylamino]acetamido]-7α-formamido-3-(pyridinium)-methyl-ceph-3-em-4-carboxylate.

* * * * *